(12) United States Patent
Gedet et al.

(10) Patent No.: US 9,055,969 B2
(45) Date of Patent: Jun. 16, 2015

(54) APPARATUS AND METHOD FOR ELONGATING A TENDON

(75) Inventors: Philippe Gedet, Oberdorf (CH);
Andreas Appenzeller, Oberdorf (CH);
Daniel Fluri, Oberdorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 328 days.

(21) Appl. No.: 13/301,384

(22) Filed: Nov. 21, 2011

(65) Prior Publication Data

US 2012/0143232 A1 Jun. 7, 2012

Related U.S. Application Data

(60) Provisional application No. 61/419,143, filed on Dec. 2, 2010.

(51) Int. Cl.
| | | |
|---|---|---|
| *A61B 17/3209* | (2006.01) | |
| *A61B 17/32* | (2006.01) | |
| *A61B 19/00* | (2006.01) | |

(52) U.S. Cl.
CPC ..... *A61B 17/3209* (2013.01); *A61B 17/320016* (2013.01); *A61B 2017/320052* (2013.01); *A61B 2019/306* (2013.01)

(58) Field of Classification Search
CPC ........... A61C 2017/320052; A61B 17/320016; A61B 17/3209; A61B 2019/306
USPC .............. 606/167, 170, 151, 213, 79; 30/282, 30/286
See application file for complete search history.

(56) References Cited

U.S. PATENT DOCUMENTS

| | | | |
|---|---|---|---|
| 4,073,060 A | | 2/1978 | Hendricks |
| 5,306,284 A | * | 4/1994 | Agee et al. .................... 606/170 |
| 5,830,221 A | * | 11/1998 | Stein et al. .................... 606/157 |
| 6,171,040 B1 | | 1/2001 | Sato |
| 7,223,275 B2 | * | 5/2007 | Shiuey ......................... 606/166 |
| 7,806,871 B2 | * | 10/2010 | Li et al. .................... 604/164.06 |
| 2004/0098005 A1 | * | 5/2004 | Mirza et al. .................... 606/170 |
| 2007/0225737 A1 | * | 9/2007 | Messerly et al. .............. 606/151 |
| 2007/0288043 A1 | * | 12/2007 | Rehnke ......................... 606/170 |
| 2008/0045989 A1 | | 2/2008 | Welborn |

FOREIGN PATENT DOCUMENTS

| | | |
|---|---|---|
| EP | 1 836 971 | 9/2007 |
| RU | 2 136 232 | 9/1999 |
| RU | 2 286 737 | 5/2006 |
| RU | 2004 133 994 | 5/2006 |

OTHER PUBLICATIONS

International Search Report and Written Opinion (PCT/US2011/061706); Apr. 3, 2012.

* cited by examiner

*Primary Examiner* — Thomas McEvoy
*Assistant Examiner* — Julie A Szpira
(74) *Attorney, Agent, or Firm* — Dunlap Codding, P.C.

(57) ABSTRACT

An apparatus and method for elongating a tendon including a cutting blade and a cutting guide supporting the cutting blade in such a way that the cutting blade is movable through at least a portion of a tendon in a helical path so as to make a helical cut in the tendon which allows elongation of the tendon.

9 Claims, 9 Drawing Sheets

APPARATUS AND METHOD FOR ELONGATING A TENDON

CROSS REFERENCE TO RELATED APPLICATION

The present application claims benefit of U.S. Provisional Application No. 61/419,143, filed Dec. 2, 2010, which is hereby incorporated herein by reference in its entirety.

BACKGROUND OF THE INVENTION

1. Field of the Inventive Concepts

The inventive concepts disclosed herein generally relate to an apparatus and method for cutting a tendon in order to achieve a lengthening thereof without a continuous cut through the tendon. More particularly, the inventive concepts relate to an apparatus which allows a helical or spiral cutting of a tendon. The inventive concepts disclosed herein also relate to a method for lengthening a tendon by helical or spiral cutting.

2. Brief Description of Related Art

Additional tendon length is occasionally needed for the surgical reattachment of a retracted tendon and for the lengthening of an intact but contracted tendon. To achieve additional tendon length using established techniques, such as z-plasty, the tendon is completely transected into two parts, loses continuity and has to be sewn back together at a selected length.

Thus, a need exists for an improved instrument and method for the operative elongation of tendons overcoming the above disadvantages. It is to such an instrument and method that the inventive concepts disclosed herein are directed.

DETAILED DESCRIPTION OF EXEMPLARY EMBODIMENTS

Figure 1:
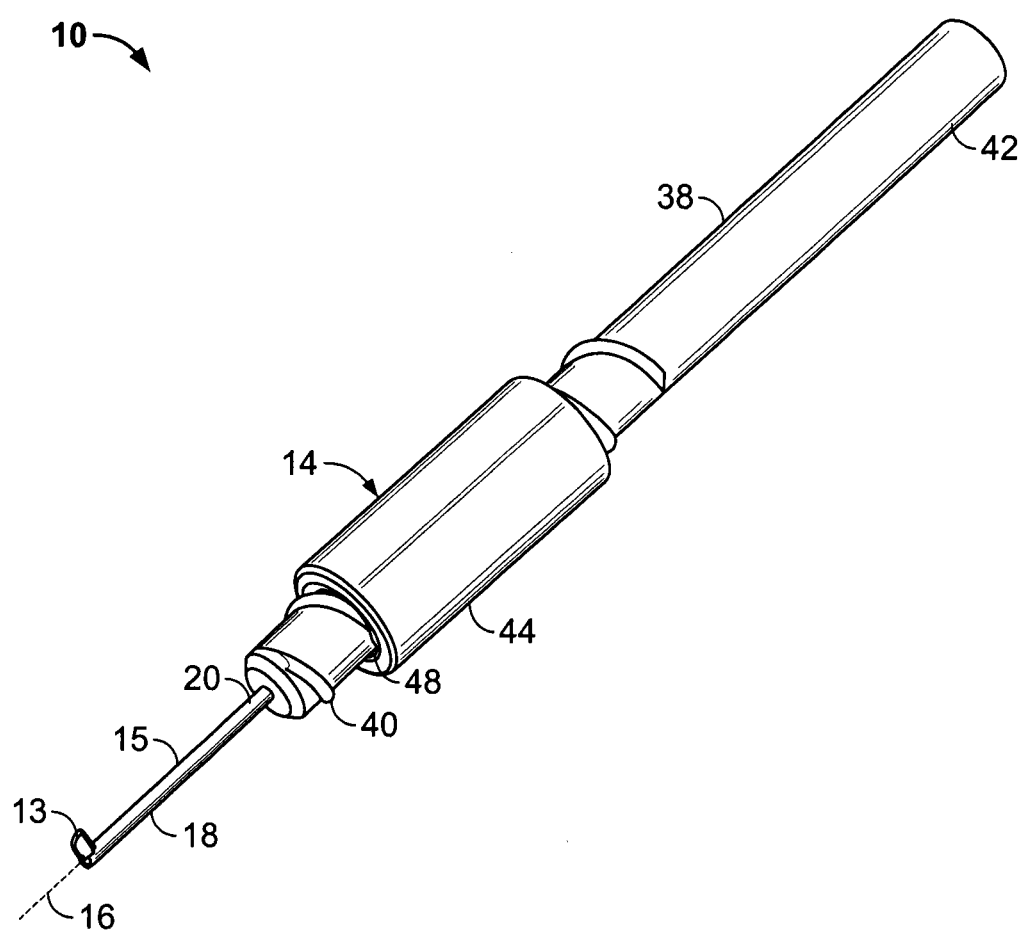
FIG. 1 is a perspective view of one embodiment of an apparatus constructed in accordance with the inventive concepts disclosed herein.

Before explaining at least one embodiment of the inventive concepts in detail, it is to be understood that the inventive concepts disclosed herein are not limited in its application to the details of construction, experiments, exemplary data, and the arrangement of the components set forth in the following description or illustrated in the drawings. The inventive concepts are capable of other embodiments or being practiced or carried out in various ways. Also, it is to be understood that the phraseology and terminology employed herein is for purposes of description and should not be regarded as limiting.

Referring now to the drawings, and more particularly to FIGS. 1-5, one embodiment of an apparatus 10 for cutting soft tissue, such as a tendon 12 (FIGS. 8 and 9) is illustrated. The apparatus 10 includes a cutting blade 13 and a cutting guide 14 for guiding the cutting blade 13 along the tendon in a helical path. The cutting guide 14 comprises a shaft 15 with a diameter d, a longitudinal axis 16, a front end 18, and a rear end 20. The shaft 15 is provided with a groove 22 near the front end 18 of the shaft 15. The groove 22 is formed so that cutting blade 13 is supported at the front end 18 of the shaft 15 so as to protrude unilaterally from the shaft 15.

The cutting blade 13 has a cutting edge 24 extending from a front face 26 at the front end 18 of the shaft 15. The cutting edge 24 increases its distance to the longitudinal axis 16 in a direction towards the rear end 20 of the shaft 15. Further, the blade 13 has a middle plane 28 (FIG. 4) which forms an angle $\alpha$ of exemplarily 45° with the longitudinal axis 16 of the shaft 15. However, it should be understood that the angle $\alpha$ may be in a range from about 20° to about 70°.

Figure 2A:
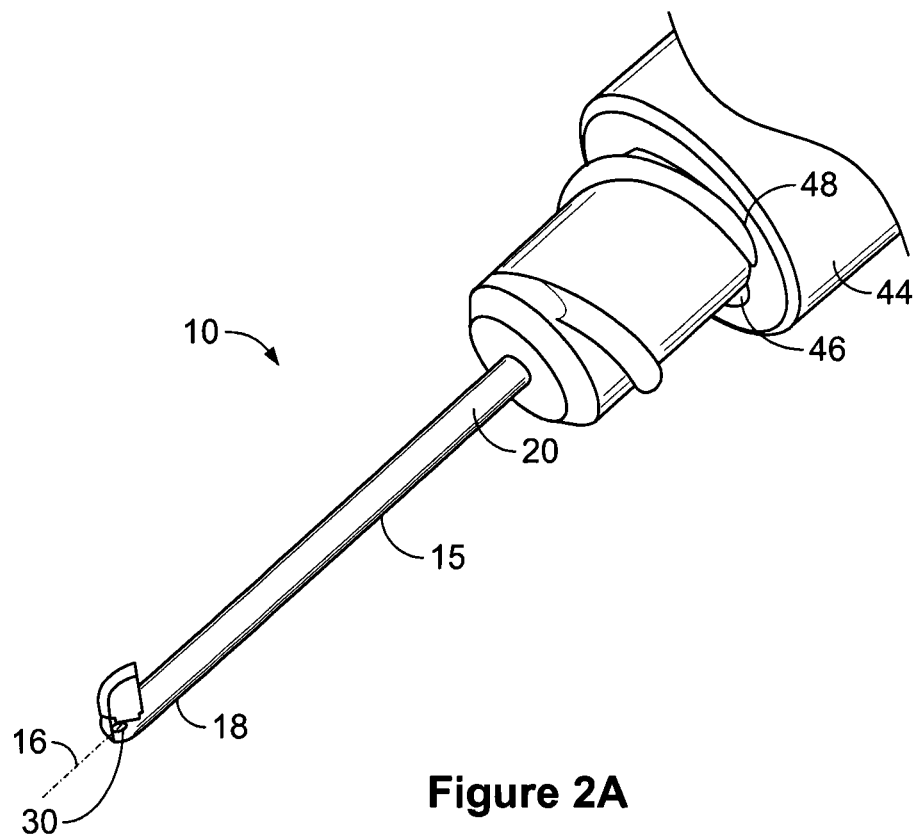
FIG. 2A is an enlarged perspective view of a portion of the apparatus of FIG. 1.
Figure 2B:
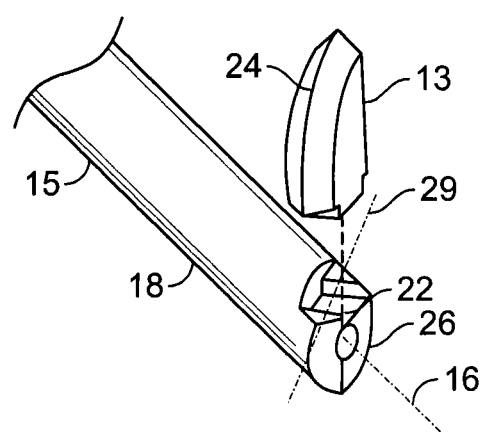
FIG. 2B is an exploded, perspective view of a portion of the apparatus of FIG. 1.
Figure 3:
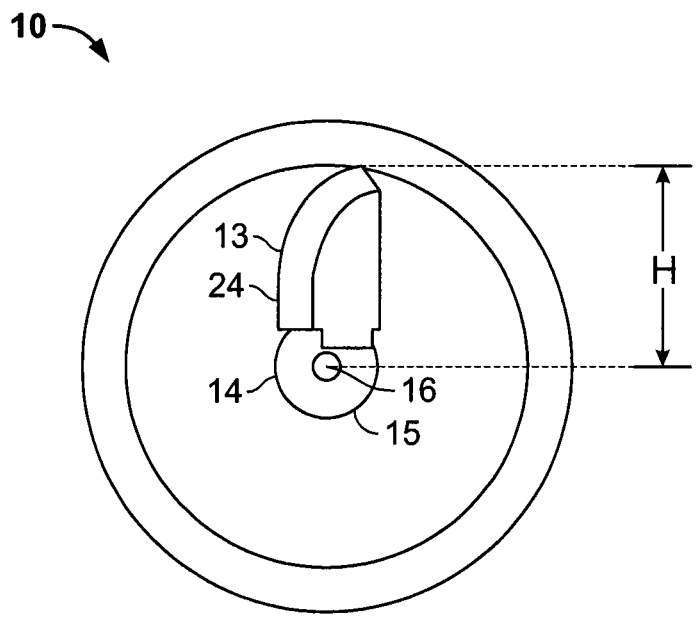
FIG. 3 is a front end view of the apparatus of FIG. 1.

As illustrated in FIG. 2B, the groove 22 has a central axis 29 extending along the length of the groove 22. The groove 22 is arranged in such a way that the central axis 29 of the groove 22 and the longitudinal axis 16 of the shaft 15 are skew lines. Further, the central axis 29 of the groove 22 forms the identical angle $\alpha$ with the longitudinal axis 16 of the shaft 15 as the middle plane 28 of the blade 13 (FIG. 4).

Figure 4:
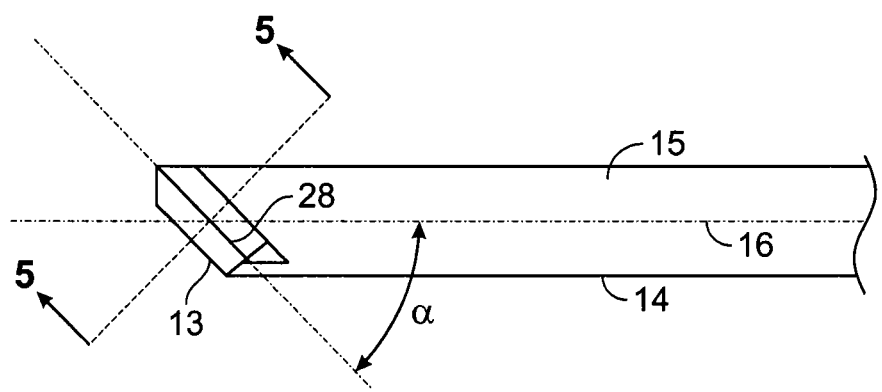
FIG. 4 is a top plan view of a front portion of the apparatus of FIG. 1.
Figure 5:
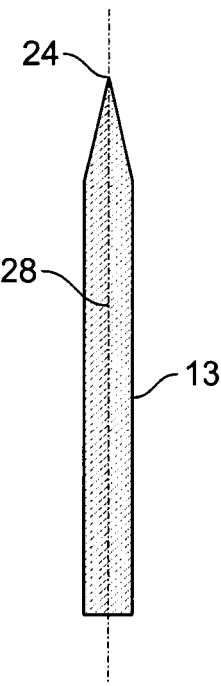
FIG. 5 is a sectional view along line 5-5 of FIG. 4.
Figure 6:
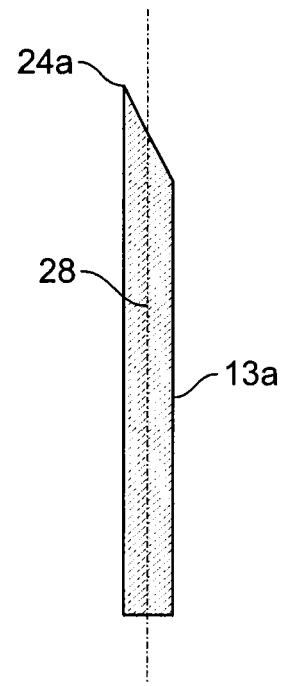
FIG. 6 is sectional view of another embodiment of a cutting blade.

As illustrated in FIG. 5, the blade 13 may be symmetrical in a cross-section along line 5-5 in FIG. 4 so that the cutting edge 24 lies in the middle plane 28 of the blade 13. Alternatively, as illustrated in FIG. 6, a blade 13a can be asymmetrical in a cross-section so that the cutting edge 24a lies in a plane which is parallel to the middle plane of the blade 13a and which coincides with one lateral surface of the blade 13.

The cutting edge 24 of the blade 13 extends to a height H from the longitudinal axis 16 measured orthogonal to the longitudinal axis 16 of the shaft 15 and to a length L measured in the middle plane 28 orthogonal to the height H. The height H is dimensioned to cut a tendon 12 with a diameter of about 2×H. The cutting edge 24 curvedly extends from the shaft 15 on a plane curve which defines a plane coinciding with the middle plane 28 of the blade 13. In one embodiment, the maximum ratio of L/H is about 0.70

Figure 8:
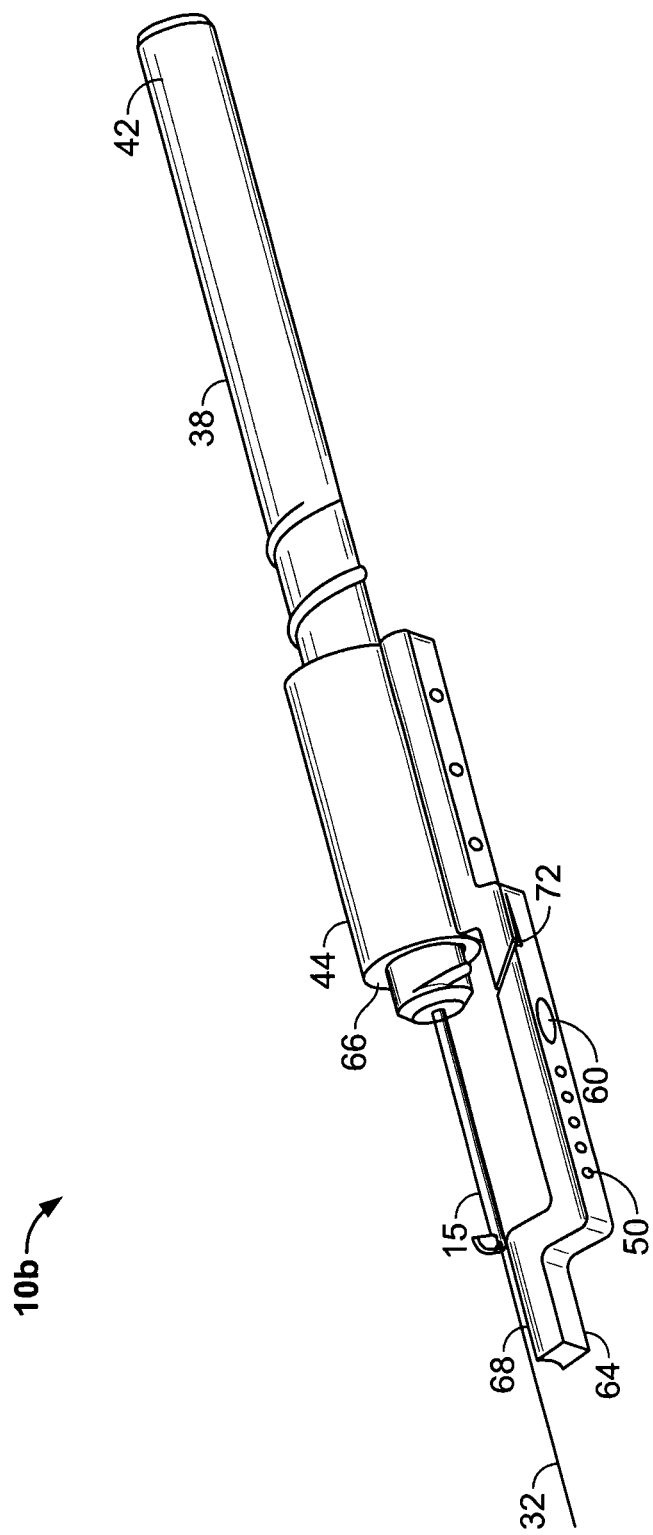
FIG. 8 is a perspective view of another embodiment of an apparatus constructed in accordance with the inventive concepts disclosed herein.
Figure 9:
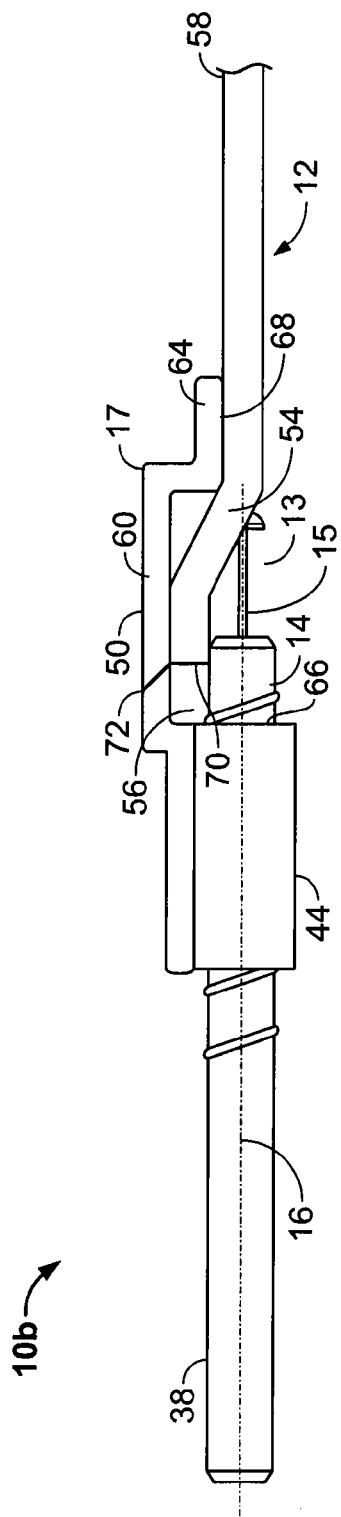
FIG. 9 is an elevational view of the apparatus of FIG. 8 shown attached to a tendon.

The shaft 15 is provided with a cannula 30 (FIGS. 2A and 3) so that the shaft 15 can be slid over and rotated about a K-wire 32 (FIG. 8) which is positioned in the tendon 12 (FIG. 9). The shaft 15 also includes an axial extension 38 extending from the rear end 20 of the shaft 15. The axial extension 38 is provided with a first helical engagement member 40 extending along the longitudinal axis 16 of the shaft 15. The axial extension 38 has a diameter D which is larger than the diameter d of the shaft 15 and has a handle 42 at its rearmost portion. The first helical engagement member 40 is configured as a helical ridge having a helix angle with respect to a plane orthogonal to the longitudinal axis 16 of the shaft 15 (FIG. 1) wherein the helix angle corresponds to the angle α between the middle plane 28 of the blade 13 and the longitudinal axis 16 of the shaft 15.

The cutting guide 14 further comprises a sleeve 44 with a central opening 46 for receiving the axial extension 38 of the shaft 15. The sleeve 44 is provided with a second helical engagement member 48 (FIG. 2A) which is engageable with the first helical engagement member 40 of the axial extension 38. The second engagement member 48 is configured as a helical groove in the inner wall of the sleeve 44. Thereby, the first and second helical engagement members 40, 48 mate with each other allowing the shaft 15 to move axially relative to the sleeve 44 upon a relative rotation.

Figure 7:
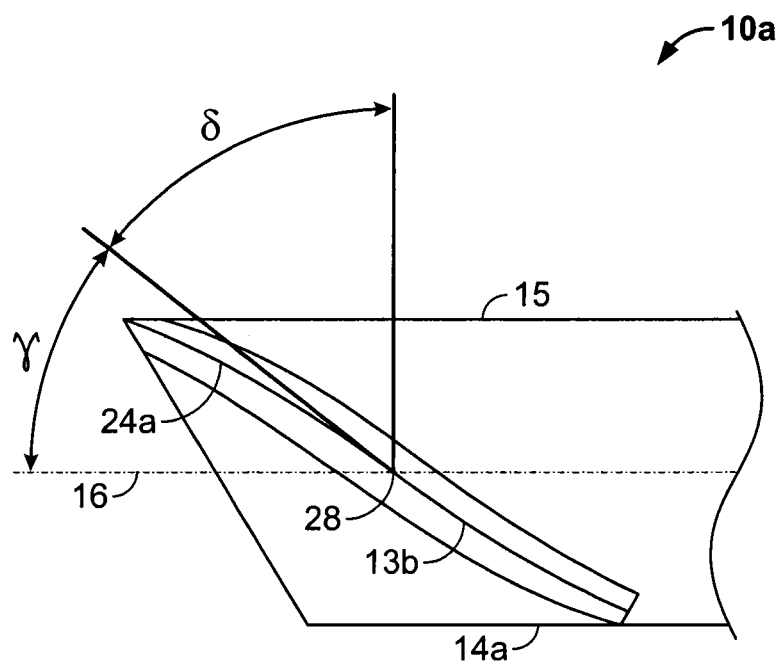
FIG. 7 is a top plan view of a front portion of another embodiment of an apparatus constructed in accordance with the inventive concepts disclosed herein.

FIG. 7 illustrates an alternative embodiment of an instrument 10a which differs from the embodiment of FIGS. 1-5 as described below. A blade 13b is incorporated as part of a cutting guide 14a. The blade 13b is a helically twisted band with a helix angle δ between the middle plane 28 of the blade 13b and a plane orthogonal to the longitudinal axis 16 of the shaft 15 wherein the angle δ is complementary to the angle γ between the middle plane 28 of the blade 13b and the longitudinal axis 16 of the shaft 15. The middle plane 28 is a helically twisted plane. The blade 13b has a cutting edge 13a extending in the helically twisted middle plane 28 of the blade 13b and has a distance to the longitudinal axis 16 of the shaft 15 which continuously increases from the foremost point of the cutting edge 24b at the front end 18 of the shaft 15 to the rearmost point of the cutting edge 24b.

FIGS. 8 and 9 illustrate another embodiment of an apparatus 10b which differs from the embodiments of FIGS. 1-5 and 7 as described below. More specifically, the apparatus 10b further comprises an adapter 50 which is attached to the sleeve 44. The adapter 50 is configured to support the tendon 12 in a bent condition along a section 54 adjacent to a fixed end 56 of the tendon 12 in an S-shaped form so that a longitudinal section 58 of the tendon 12 is shifted with respect to the fixed end 56 of the tendon 12. The adapter 50 is an elongated member extending along the longitudinal axis 16 of the shaft 15 and protruding distally from the sleeve 44 so as to form an extension arm 60 providing a first support surface and a second support surface longitudinally and laterally spaced from one another to which a section 54 of the tendon 12 which is adjacent the fixed end 56 of the tendon 12 can be affixed. At a front 66 of the sleeve 44, the adapter 50 is stepped away from the longitudinal axis 16 of the shaft 15, so that the adapter 50 can be fixed to the section 54 of the tendon 12 which is adjacent to the fixed end 56 of the tendon 12 in such a way that the axial extension 38 of the shaft 15 can be lead beside the fixed end 56 of the tendon 12 and towards the longitudinal section 58 of the tendon 12 to be treated.

The adapter 50 has a nose 64 located at the free end of the adapter 50. The nose 64 has a contact surface 68 which is spaced apart from the longitudinal axis 16 of the shaft 15 about half of the diameter of the tendon 12, so that the longitudinal section 58 of the tendon 12 that abuts the contact surface 68 comes at rest essentially coaxial to the longitudinal axis 16 of the shaft 15. The apparatus 10b is fixed to the tendon 12 by means of a fastener, such as a suture 70, in the proximity of the fixed end 56 of the tendon 12. For this purpose, the suture 70 is lead around the tendon 12 and fixed in two notches 72 which are located on opposite lateral sides of the adapter 50. The adapter 50 is fixable to the sleeve 44 by means of two fasteners, such as screws.

Figure 10:
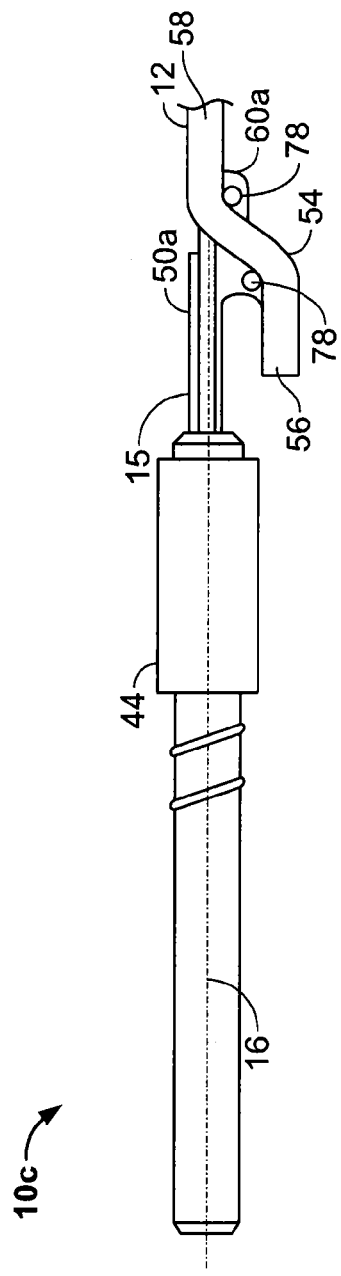
FIG. 10 is an elevational view of another embodiment of an apparatus constructed in accordance with the inventive concepts disclosed herein shown attached to a tendon.

FIG. 10 illustrates another embodiment of an apparatus 10c which differs from the embodiment of FIG. 8, as described below. More specifically, the apparatus 10c has an adapter 50a which comprises an extension arm 60a which protrudes distally from the sleeve 44 and which extends along the longitudinal axis 16 of the shaft 15. The adapter 50a comprises two pins 78 that are spaced apart from each other in a direction along the longitudinal axis 16 of the shaft 15. The pins 78 are differently spaced apart from the longitudinal axis 16 in a direction orthogonal to the longitudinal axis 16 of the shaft 15. The pins 78 can be positioned on opposite sides of the tendon 12 and the shaft 15 including the extension arm 60a can be twisted in such a way that the longitudinal section 58 of the tendon 12 comes at rest essentially coaxial to the longitudinal axis 16 of the shaft 15. Thereby, a section 54 of the tendon 12 which is located between the fixed end 56 of the tendon 12 and the longitudinal section 58 of the tendon 12 to be shifted is positioned between the two pins 78 and bent in a S-shaped form.

In use, the tendon 12 is bent on a section 54 adjacent to one of the fixed ends 56 of the tendon 12 in such a way that a longitudinal section 58 of the tendon 12 is shifted with respect to the fixed end 56 of the tendon 12. This longitudinal section 58 of the tendon 12 then extends in a direction which is offset from the natural direction of the tendon 12 and offset from the fixed end 56 of the tendon 12. Thereby, a section 54 of the tendon 12 which is located between the fixed end 56 of the tendon 12 and the longitudinal section 58 of the tendon 12 to be shifted is bent into an S-shaped form. The tendon 12 can be bent either by using tweezers or by using an embodiment of the apparatus 10a or 10b of FIGS. 8 and 10.

By using the embodiment of the apparatus 10a of FIG. 8, the tendon 12 can be fixed to the adapter 50 with a suture 70. A strand of the suture 70 which is fixed to the adapter 50 is led around the tendon 12 and can be clamped to the adapter 50 near the sleeve 44. The clamping of the suture 70 can be realized with a notch 72 located in the extension arm 60 of the adapter 50 into which the suture 70 is wedged.

By using the embodiment of the apparatus 10b of FIG. 10, the adapter 50a including pins 78 mounted on the extension arm 60 can be chosen of the size of the tendon 12. From a set of pins 78 with different diameters, two pins 78 can be selected to adapt the adapter 50a to the respective tendon 12. A section 54 of the tendon 12 which is located between the fixed end 56 of the tendon 12 and the longitudinal section 58 of the tendon 12 to be shifted is positioned between the two pins 78 and bent in an S-shaped form by twisting the apparatus 10 about an axis transverse to the longitudinal axis 16 of the shaft 15.

In a second step, a K-wire 32 is inserted into the shifted longitudinal section 58 of the tendon 12 in a direction essentially coaxial with the central axis of the shifted longitudinal section 58 of the tendon 12.

In a third step, the shaft 15 of the apparatus 10 is slid over the K-wire 32 into the human body until the blade 13 contacts the longitudinal section 58 of the tendon 12.

After the apparatus 10 has been correctly positioned, the shaft 15 is rotated about its longitudinal axis 16 and simultaneously axially advanced through the shifted longitudinal section 58 of the tendon 12 in a helical path to thereby make a helical cut into the tendon 12 by means of the cutting edge 24. By holding the sleeve 44 in a fixed position relative to the tendon 12 and turning the shaft 15 clockwise, the blade 13 moves towards the tendon 12. As a result of the number of turns and the cutting angle α with its corresponding pitch, the length of the helix can be defined. After having achieved the desired length of the helix, the blade 13 can be reversed without injuring the tissue because the back side of the blade 13 is blunt.

Figure 11:
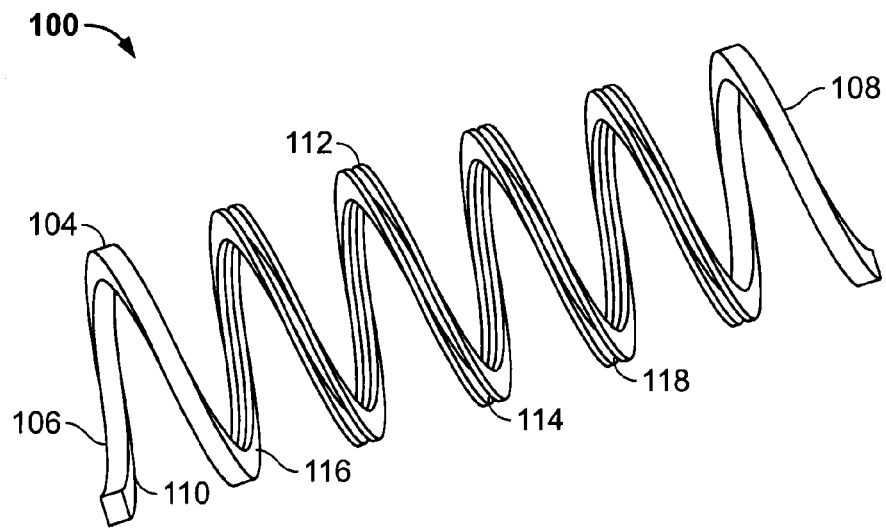
FIG. 11 is a perspective view of a cutting guide constructed in accordance with the inventive concepts disclosed herein.
Figure 12:
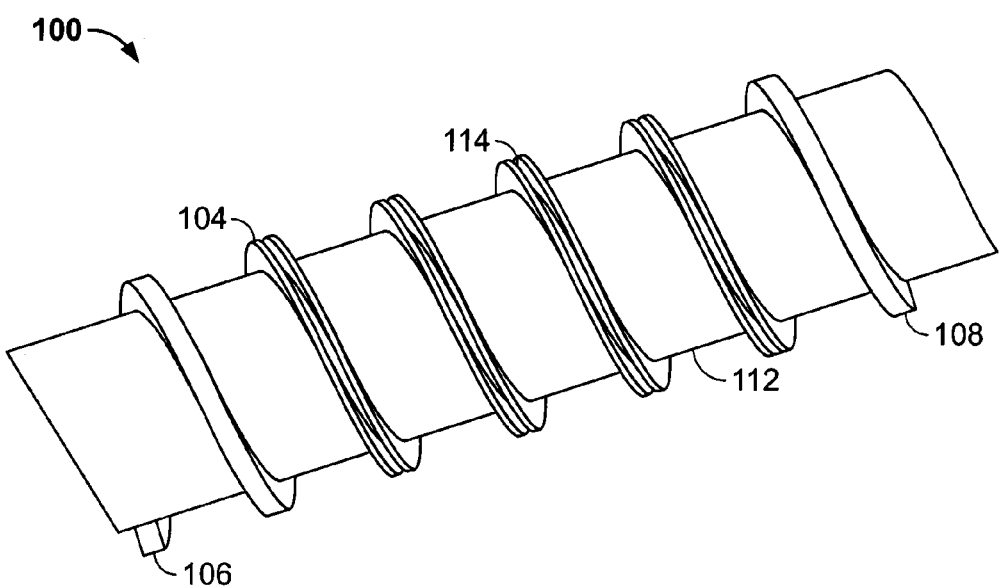
FIG. 12 is a perspective view of the cutting guide of FIG. 11 shown positioned about a tendon.
Figure 13:
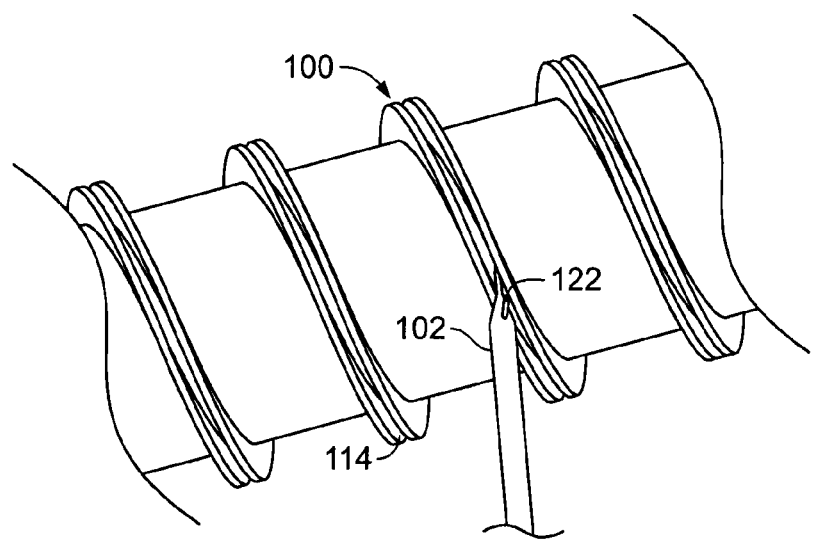
FIG. 13 is a perspective view showing a cutting blade being guided by the cutting guide of FIG. 11.

Referring now to FIGS. 11-13, another embodiment of a cutting guide 100 is illustrated. The cutting guide 100 is to be used in combination with a blade, such as a blade 102 (FIG. 13), for making a helical cut along a portion of a tendon. The cutting guide 100 includes a helical body 104. The helical body 104 has a first end 106, a second end 108, an interior side 110, and an exterior side 112.

The helical body 104 has a blade receiving slot 114 extending through the helical body 104 from the exterior side 112 to the interior side 110. The blade receiving slot 114 is dimensioned to slidably receive a blade, such as the blade 102. Further, the blade receiving slot 114 illustrated in FIG. 11 has a closed first end 116 and a closed second end 118, but it will be appreciated that one of the ends of the blade receiving slot 114 may be open.

To facilitate positioning the helical body 104 about a tendon, the first end 106 and the second end 108 of the helical body 104 are open in such a way that the helical body 104 may be rotated about a segment of a tendon to position the helical body 104 about the tendon as shown in FIG. 12. It will be appreciated by those of ordinary skill in the art that the helical body 104 may be formed from any suitable material, such as metal or plastic, and may be made using conventional methods, such as injection molding, laser melting, casting, machining, molding, and combinations thereof, for example. It will also be appreciated that the helical body 104 may be constructed in a variety of lengths and widths and with a variety of helix angles.

In use, the helical body 104 is positioned about a selected section of a tendon 12 by rotating the helical body 104 about the tendon. A surgeon then utilizes a cutting blade, such as the cutting blade 102, and the cutting guide 100 to make a helical cut in the tendon. The cutting blade 102 may be provided with a stop member 122 that contacts the exterior side 112 of the helical body 104 to limit the depth which the cutting blade 102 can penetrate into the tendon 12. It will be appreciated by those of ordinary skill in the art the limit to depth can be any depth suitable to achieve a desired tendon elongation. A preferred limit to the depth may be, limiting the cutting to the center of the tendon. Once the desired cut in the tendon 12 has been made, the helical body 104 may be removed from the tendon 12.

Figure 14:
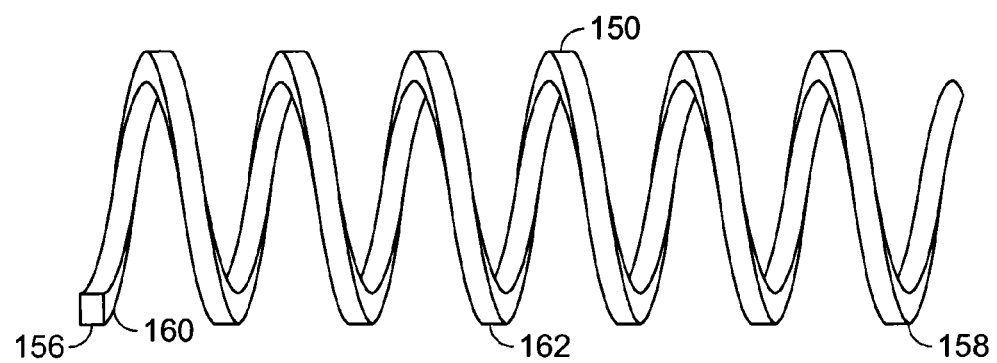
FIG. 14 is a perspective view of another embodiment of a cutting guide constructed in accordance with the inventive concepts disclosed herein.
Figure 15:
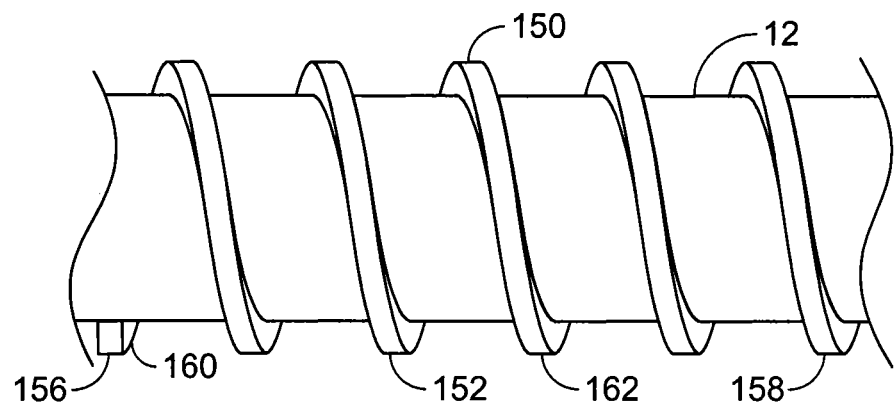
FIG. 15 is a perspective view of the cutting guide of FIG. 14 shown positioned about a tendon.
Figure 16:
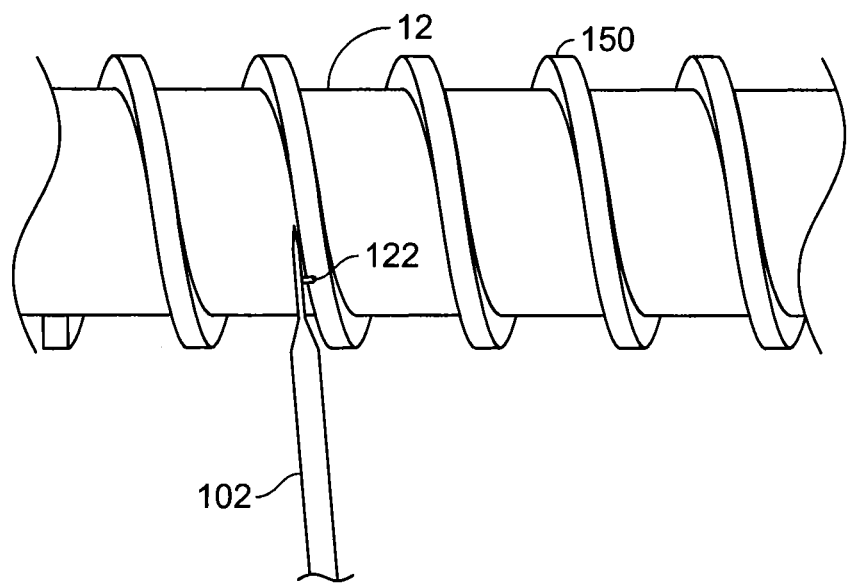
FIG. 16 is a perspective view showing a cutting blade being guided by the cutting guide of FIG. 14.

FIGS. 14-16 illustrate another embodiment of a cutting guide 150. The cutting guide 150 is to be used in combination with a blade, such as a blade 102 (FIG. 16), for making a helical cut along a portion of a tendon. The cutting guide 150 includes a helical body 152. The helical body 152 has a first end 156, a second end 158, an interior side 160, and an exterior side 162.

To facilitate positioning the helical body 152 about a tendon, the first end 156 and the second end 158 of the helical body 152 are open in such a way that the helical body 152 may be rotated about a segment of a tendon to position the helical body 152 about the tendon as shown in FIG. 15. It will be appreciated by those of ordinary skill in the art that the helical body 152 may be formed from any suitable material, such as metal or plastic, and may be made using conventional methods, such as injection molding, laser melting, casting, machining, molding, and combinations thereof, for example. It will also be appreciated that the helical body 152 may be constructed in a variety of lengths and widths.

In use, the cutting guide 150 is used in a manner similar to the cutting guide 100 described above, except a surgeon moves the cutting blade 102 along one side of the helical body 152 until the desired but has been made. The cutting blade 102 may again include the stop member 122 that contacts exterior side 162 of the helical body 152 to limit the depth which the cutting blade 102 penetrates the tendon.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and/or as defined in the appended claims.

What is claimed is:

1. An apparatus for cutting a tendon, comprising: a cutting blade; and
    a cutting guide supporting the cutting blade in such a way that the cutting blade is movable through at least a portion of the tendon in a helical path so as to make a helical cut in the tendon, wherein the cutting guide comprises a helical body having a first end, a second end, an interior side, and an exterior side; the helical body having a blade receiving slot extending through the helical body from the exterior side to the interior, side, wherein the blade receiving slot has a closed first end and a closed second end.

2. The apparatus of claim 1, wherein the first end and the second end of the helical body are open in such a way that the helical body may be rotated about a tendon to position the helical body about the tendon.

3. An apparatus for cutting a tendon, comprising: a cutting blade; and
    a cutting guide supporting the cutting blade in such a way that the cutting blade is movable through at least a portion of the tendon in a helical path so as to make a helical cut in the tendon, wherein the cutting guide comprises a shaft having a front end, a rear end, a longitudinal axis, and a cannula extending through the shaft from the front end to the rear end along the longitudinal axis, the shaft having a first helical engagement member extending along a portion of the shaft and having a helix angle β with respect to a plane orthogonal to the longitudinal axis of the shaft; and
    a sleeve with a central opening for receiving a portion of the shaft, the sleeving having a second helical engagement member which is matingly engaged engageable with the first helical engagement member of the shaft in such a way as to cause axial movement of the shaft in response to rotation of the shaft relative to the sleeve,
    wherein the cutting blade has a cutting edge, the cutting blade extending laterally from the shaft with the cutting blade extending from the front end of the shaft and the cutting blade disposed at an angle α with respect to the longitudinal axis of the shaft, the angle a corresponding to the helix angle β.

4. The apparatus of claim 3, wherein the cutting edge is curved.

5. The apparatus of claim 4, wherein the cutting edge extends from front end of the shaft toward the rear end of the shaft.

6. The apparatus of claim 3 wherein the cutting edge of the cutting blade extends along the shaft from the front end toward the rear end in a helical configuration.

7. The apparatus of claim 3, wherein the cutting guide further comprises:
   an adapter attached to the sleeve and comprising an extension arm extending from the sleeve toward the front end of the shaft, the extension arm having a first support surface and a second support surface longitudinally and laterally spaced from one another in such a way as to support a portion of a tendon in an S-shaped form.

8. The apparatus of claim 7, wherein one of the support surfaces of the extension arm is defined by a nose located at a free end of the adapter and wherein other support surface is defined by a portion of the extension arm spaced apart from the longitudinal axis of the shaft in a direction orthogonal to the longitudinal axis, the nose is stepped towards the longitudinal axis so as to allow the portion of the tendon to be bent in such a way that the longitudinal axis of the shaft is alignable with a longitudinal axis of a section of the tendon which is adjacent to the end portion of the tendon.

9. The apparatus of claim 7, the support surfaces of the extension arm is defined by a pair of pins spaced apart from each other in a direction along the longitudinal axis of the shaft and spaced apart from the longitudinal axis in a direction orthogonal to the longitudinal axis.

* * * * *